(12) United States Patent
Snyder et al.

(10) Patent No.: US 6,767,875 B1
(45) Date of Patent: Jul. 27, 2004

(54) HAIR CONDITIONING COMPOSITION COMPRISING CARBOXYLIC ACID/ CARBOXYLATE COPOLYMER AND MOISTURIZING AGENT

(75) Inventors: Michael Albert Snyder, Kobe (JP); Jian-Zhong Yang, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/070,199

(22) PCT Filed: Sep. 3, 1999

(86) PCT No.: PCT/US99/20109
§ 371 (c)(1),
(2), (4) Date: Mar. 4, 2002

(87) PCT Pub. No.: WO01/17489
PCT Pub. Date: Mar. 15, 2001

(51) Int. Cl.[7] .......................... A61K 7/06; A61K 7/075; C11D 3/37; C11D 3/20; C11D 13/10
(52) U.S. Cl. ................. 510/119; 510/121; 510/122; 510/421; 510/434; 510/466; 510/475; 510/476; 510/477; 510/488; 424/401; 424/70.1; 424/70.12; 424/70.16; 424/70.31
(58) Field of Search .................... 510/119, 121, 510/122, 421, 434, 466, 475, 476, 477, 488; 424/401, 70.1, 70.12, 70.16, 70.31

(56) References Cited
U.S. PATENT DOCUMENTS 5,344,643 A * 9/1994 Thiel et al. ................. 424/70

FOREIGN PATENT DOCUMENTS

| FR | 2 748 932 A | | 11/1997 | |
|---|---|---|---|---|
| FR | 2748932 | * | 11/1997 | ............ A61K/7/13 |
| GB | 2 315 771 A | | 2/1998 | |
| GB | 2315771 | * | 2/1998 | ............ A61K/7/15 |
| JP | 90 077641 A | | 3/1997 | |
| WO | WO 92/05234 | * | 4/1992 | ............ C11D/1/10 |
| WO | WO-92/19216 A1 | | 11/1992 | |
| WO | WO-99/24010 A1 | | 5/1999 | |
| WO | WO 99/24010 | * | 5/1999 | ............ A61K/7/48 |
| WO | WO 00/06089 | * | 2/2000 | ............ A61K/7/00 |
| WO | WO-00/06089 A1 | | 2/2000 | |
| WO | WO 00/06090 | * | 2/2000 | ............ A61K/7/00 |
| WO | WO-00/06090 A1 | | 2/2000 | |
| WO | WO-00/06097 A1 | | 2/2000 | |
| WO | WO 00/06097 | * | 2/2000 | ............ A61K/7/06 |
| WO | WO-00/06098 A1 | | 2/2000 | |
| WO | WO 00/06098 | * | 2/2000 | ............ A61K/7/06 |
| WO | WO 01/17489 | * | 3/2001 | ............ A61K/7/06 |

* cited by examiner

Primary Examiner—Brian P. Mruk
(74) Attorney, Agent, or Firm—Linda M. Sivik; Tara M. Rosnell

(57) ABSTRACT

Disclosed is a hair conditioning composition comprising: (1) from about 0.01% to about 10% of a carboxylic acid/ carboxylate copolymer; (2) from about 0.1% to about 10% of a moisturizing agent selected from the group consisting of a polypropylene glycol, an alkyl ethoxylate, and mixtures thereof; and (3) an aqueous carrier. Further disclosed is a method of making such hair conditioning compositions.

8 Claims, No Drawings

HAIR CONDITIONING COMPOSITION COMPRISING CARBOXYLIC ACID/ CARBOXYLATE COPOLYMER AND MOISTURIZING AGENT

TECHNICAL FIELD

The present invention relates to hair conditioning compositions comprising a carboxylic acid/carboxylate copolymer and a moisturizing agent selected from the group consisting of a polypropylene glycol and an alkyl ethoxylate.

BACKGROUND

Human hair becomes soiled due to its contact with the surrounding environment and from serum secreted by the scalp. The soiling of the hair causes it to have a dirty or greasy feel, and an unattractive appearance. The soiling of the hair necessitates shampooing with regularity.

Shampooing deans the hair by removing excess soil and serum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying which can interfere with combing and result in a condition commonly referred to as "fly-away hair", or contribute to an undesirable phenomena of "split ends", particularly for long hair.

A variety of approaches have been developed to alleviate these after-shampoo problems. These approaches range from post-shampoo application of hair conditioner such as leave-on and rinse-off products, to hair conditioning shampoos which attempt to both cleanse and condition the hair from a single product. Although some consumers prefer the ease and convenience of a shampoo which includes conditioners, a substantial proportion of consumers prefer the more conventional conditioner formulations which are applied to the hair as a separate step from shampooing, usually subsequent to shampooing. Such consumers who prefer the conventional conditioner formulations value the relatively higher conditioning effect, or convenience of changing the amount of conditioning depending on the condition of hair or portion of hair.

Conditioning formulations can be in the form of rinse-off products or leave-on products, and can be in the form of an emulsion, cream, gel, spray, and mousse. Products in the form of cream, gel, and mousse are suitable in that the consumer can easily control the amount and distribution of the product. As such, these products are particularly suitable for leave-on products. Leave-on products which do not leave the hands with a tacky, dirty, feeling is desired.

Co-pending PCT applications US98/15852, US98/15853, US98/15854, and US98115855, describe hair care compositions suitable for leave-on products which contain a carboxylic acid/carboxylate copolymer. While such compositions are suitable for leave-on use, provide hair feel such as smoothness, softness, and reduction of friction, are easy to apply on the hair, and leave the hair and hands with a clean feeling, they are not satisfactory in providing moisturized hair at is feel and reduction of bulk hair volume. Fly-away hair is due to the increased level of static, and represents volume increase of only very minor amount of the hair as a whole, and is not desirable. On the other hand, reduction of hair volume as used herein relates to reduction of the bulk of the hair volume.

Based on the foregoing, there remains a desire to provide hair conditioning compositions suitable for leave-on use which provide improved conditioning benefits to the hair such as moisturized feel, reduction of bulk hair volume, are easy to apply on the hair, and leave the hair and hands with a clean feeling.

None of the existing art provides all of the advantages and benefits of the present invention.

SUMMARY

The present invention is directed to a hair conditioning composition comprising:

(1) from about 0.01% to about 10% of a carboxylic acid/carboxylate copolymer;

(2) from about 0.1% to about 10% of a moisturizing agent selected from the group consisting of a polypropyleneglycol, an alkyl ethoxylate, and mixtures thereof; and (3) an aqueous carrier.

The present invention is further directed to a method of making the hair conditioning composition described above.

These and other features, aspects, and advantages of the present invention will become evident to those skilled in the art from a reading of the present disclosure.

DETAILED DESCRIPTION

While the specification concludes with claims which particularly point out and distinctly claim the invention, it is believed the present invention will be better understood from the following description.

All cited references are incorporated herein by reference in their entireties. Citation of any reference is not an admission regarding any determination as to its availability as prior art to the claimed invention.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

The aspects and embodiments of the present invention set forth in this document have many advantages. For example, the hair conditioning compositions of the present invention provide: a product suitable for leave-on use which provide improved conditioning benefits to the hair such as moisturized feel, reduction of bulk hair volume, are easy to apply on the hair, and leave the hair and hands with a clean feeling.

CARBOXYLIC ACID/CARBOXYLATE COPOLYMER

The compositions of the present invention comprise an carboxylic acid/carboxylate copolymer. The carboxylic acid/carboxylate copolymers herein are hydrophobically-modified cross-linked copolymers of carboxylic acid and alkyl carboxylate, and have an amphiphilic property. These carboxylic acid/carboxylate copolymers are obtained by copolymerizing 1) a carboxylic acid monomer such as acrylic acid, methacrylic acid, maleic acid, maleic anhydride, itaconic acid, fumaric acid, crotonic acid, or α-chloroacrylic acid, 2) a carboxylic ester having an alkyl chain of from 1 to about 30 carbons, and preferably 3) a crosslinking agent of the following formula:

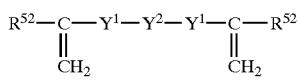

wherein $R^{52}$ is a hydrogen or an alkyl group having from about 1 to about 30 carbons; $Y^1$, independently, is oxygen, $CH_2O$, COO, OCO,

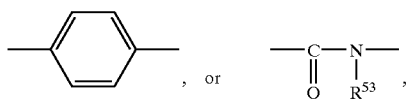

wherein $R^{53}$ is a hydrogen or an alkyl group having from about 1 to about 30 carbons; and $Y^2$ is selected from $(CH_2)_{m''}$, $(CH_2CH_2O)_{m''}$, or $(CH_2CH_2CH_2O)_{m''}$ wherein m" is an integer of from 1 to about 30. The carboxylic acid/carboxylate copolymers herein are believed to provide appropriate viscosity and rheology properties to the composition, and to emulsify and stabilize certain conditioning agents in the composition. It is further believed that, because of the alkyl group contained in the copolymer, the carboxylic acid/carboxylate copolymers do not make the composition undesirably sticky.

The composition of the present invention preferably comprises the carboxylic acid/carboxylate copolymer at a level by weight of from about 0.01% to about 10%, more preferably from about 0.1% to about 2%.

Suitable carboxylic acid/carboxylate copolymers herein are acrylic acid/alkyl acrylate copolymers having the following formula:

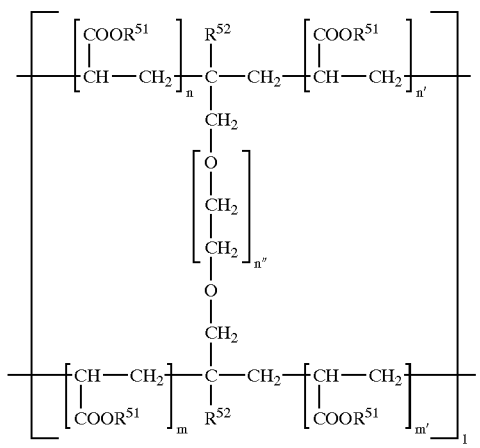

wherein $R^{51}$, independently, is a hydrogen or an alkyl of 1 to 30 carbons wherein at least one of $R^{51}$ is a hydrogen, $R^{52}$ is as defined above, n, n', m and m' are integers in which n+n'+m+m' is from about 40 to about 100, n" is an integer of from 1 to about 30, and l is defined so that the copolymer has a molecular weight of about 500,000 to about 3,000,000.

Commercially available carboxylic acid/carboxylate copolymers useful herein include: CTFA name Acrylates/C10–30 Alkyl Acrylate Crosspolymer having tradenames PEMULENE TR-1, PEMULENE TR-2, CARBOPOL 1342, CARBOPOL 1382, and CARBOPOL ETD 2020, all available from B. F. Goodrich Company.

Neutralizing agents may be included to neutralize the carboxylic acid/carboxylate copolymers herein. Nonlimiting examples of such neutralizing agents include sodium hydroxide, potassium hydroxide, ammonium hydroxide, monethanolamine, diethanolamine, triethanolamine, diisopropanolamine, aminomethylpropanol, tromethamine, tetrahydroxypropyl ethylenediamine, and mixtures thereof.

Upon making the present composition, the carboxylic acid/carboxylate copolymers are preferably neutralized with the neutralizing agents prior to mixing with components which may provide an undesirable complex with the unneutralized form of the carboxylic acid/carboxylate copolymers. Components which may provide such undesirable complex are, for example, amphoteric polymers, which are discussed later in the present specification.

MOISTURIZING AGENT

The hair care composition of the present invention comprises a moisturizing agent selected from the group consisting of an alkyl ethoxylate, a polypropylene glycol, and mixtures thereof. It is believed that the moisturizing agents herein provide improved conditioning benefits to the hair such as moisturized feel and reduction of bulk hair volume. The moisturizing agent is present at a level of from about 0.1% to about 10%, and preferably from about 0.5% to about 3%, more preferably from about 1% to about 2% by weight of the hair care composition.

Alkyl Ethoxylate

The alkyl ethoxylate useful herein has the formula:

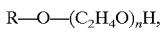

wherein R is an alkyl group having from about 1 to about 30 carbon atoms, preferably from about 6 to about 22 carbon atoms, and more preferably from about 8 to about 18 carbon atoms; R may be branched, linear, saturated, unsaturated, but is preferably linear and saturated, or unsaturated having about one double bond; n is from about 1 to about 10, preferably from about 2 to about 8, and more preferably from about 3 to about 6; the weight average molecular weight of the alkyl ethoxylate is less than about 500 g/mol, preferably from about 100 to about 500 g/mol, and more preferably from about 200 to about 500 g/mol; and the HLB value of the alkyl ethoxylate is from about 5 to about 12, preferably from about 6 to about 11, and more preferably from about 6 to about 10.

As may be seen from the HLB values, such alkyl ethoxylates are miscible in both oil and water. Furthermore, such alkyl ethoxylates typically have a melting point of less than about 30° C., preferably less than about 25° C., and more preferably less than about 20° C., and have a cloud point (1% solution) of less than about 50° C., preferably less than about 40° C., and more preferably less than about 35° C.

The HLB value is a theoretical index value which describes the hydrophilicity-hydrophobicity balance of a specific compound. Generally, it is recognized that the HLB index ranges from 0 (very hydrophobic) to 40 (very hydrophilic). The HLB value of the alkyl ethoxylate may be found in tables and charts known in the art, or may be calculated with the following general equation: HLB=7+Σ(hydrophobic group values)+Σ(hydrophilic group values). The HLB and methods for calculating the HLB of a compound are explained in detail in "Surfactant Science Series, Vol. 1: Nonionic Surfactants", pp. 606–13, M. J. Schick (Marcel Dekker, Inc., New York, 1966).

Without intending to be limited by theory, it is believed that the alkyl ethoxylates useful herein provide a bulk hair volume reduction benefit by the following mechanism: The hydrophobic alkyl chains attach to hair fibers, even under rinse-off conditions, while the hydrophilic ethoxylate groups attract water molecules and bring them to the hair fibers. This moisturizes the hair fiber, and helps maintain it in a flexible, soft, and plastic state. This in turn, allows the hair a fiber to maintain a well-aligned conformation (with respect to other hair fibers) and to easily recover from deformation. This further increases the likelihood that the hair fibers will remain parallel, and/or hang straight down. This significantly reduces the space between the individual hair fibers, and therefore reduces bulk hair volume.

Without intending to be limited by theory, it is also believed that the alkyl ethoxylate may reduce fly-away hair volume as well. By moisturizing the hair fiber, the alkyl ethoxylate may also reduce the hair fiber's static charge and crookedness. This in turn, reduces the electrostatic repulsion and space between hair fibers, which leads to a reduction in fly-away volume.

Highly preferred examples of the alkyl ethoxylate useful herein include, for example, oleth-5, oleth-3, steareth-5, steareth-4, ceteareth-5, ceteareth-4, ceteareth-3, mixtures of $C_{9-11}EO5$, mixtures of $C_{9-11}EO2.5$, mixtures of $C_{12-13}EO3$, mixtures of $C_{11-13}EO5$, and mixtures thereof. These alkyl ethoxylates are available from, for example, Croda Chemical Ltd., of Parsippany, N.J., U.S.A., Shell Chemical of U.S.A., BASF of Germany, Mitsubishi Chemical of Tokyo, Japan, and Nikko Chemical, of Tokyo, Japan. Such alkyl ethoxylates are especially preferred for use in rinse-off hair conditioning compositions.

If the hair care comparison is intended for use as a rinse-off hair conditioning composition, it is highly preferred that the alkyl ethoxylate have a cloud point of less than about 40° C. Without intending to be limited by theory, it is believed that this significantly improves the deposition efficiency of the alkyl ethoxylate onto hair.

Polypropylene Glycol

The polypropylene glycol useful herein has a weight average molecular weight of from about 200 g/mol to about 100,000 g/mol, preferably from about 1,000 g/mol to about 60,000 g/mol. Without intending to be limited by theory, it is believed that the polypropylene glycol herein deposits onto, or is absorbed into hair to act as a humectant/moisturizer, and/or provides one or more other desirable hair conditioning benefits. As used herein, the term "polypropylene glycol" includes single-polypropylene glycol-chain segment polymers, and multi-polypropylene glycol-chain segment polymers. The general structure of branched polymers such as the multi-polypropylene glycol-chain segment polymers herein are described, for example, in "Principles of Polymerization," pp. 17–19, G. Odian, (John Wiley & Sons, Inc., 3d ed., 1991).

The polypropylene glycol herein are typically polydisperse polymers. The polypropylene glycols useful herein have a polydispersity of from about 1 to about 2.5, preferably from about 1 to about 2, and more preferably from about 1 to about 1.5. As used herein, the term "polydispersity" indicates the degree of the molecular weight distribution of the polymer sample. Specifically, the polydispersity is a ratio, greater than 1, equal to the weight average molecular weight divided by the number average molecular weight. For a further discussion about polydispersity, see "Principles of Polymerization," pp. 20–24, G. Odian, (John Wiley & Sons, Inc., $3^{rd}$ ed., 1991).

The polypropylene glycol useful herein may be either water-soluble, water-insoluble, or may have a limited solubility in water, depending upon the degree of polymerization and whether other moieties are attached thereto. The desired solubility of the polypropylene glycol in water will depend in large part upon the form (e.g., leave-on, or rinse-off form) of the hair care composition. The solubility in water of the polypropylene glycol herein may be chosen by the artisan according to a variety of factors. Both water-soluble and water-insoluble polypropylene glycols are useful for leave-on form compositions. The present invention may also take the form of a rinse-off hair care composition. Without intending to be limited by theory, it is believed that in such a composition, a water-soluble polypropylene glycol may be too easily washed away before it effectively deposits on hair and provides the desired benefit(s). For such a composition, a less soluble, or even a water-insoluble polypropylene glycol is therefore preferred. Accordingly, for a rinse-off hair care composition, it is preferred that the polypropylene glycol herein has a solubility in water at 25° C. of less than about 1 g/100 g water, more preferably a solubility in water of less than about 0.5 g/100 g water, and even more preferably a solubility in water of less than about 0.1 g/100 g water.

Preferably the polypropylene glycol is selected from the group consisting of a single-polypropylene glycol-chain segment polymer, a multi-polypropylene glycol-chain segment polymer, and mixtures thereof, more preferably selected from the group consisting of a single-polypropylene glycol-chain segment polymer of Formula I, below, a multi-polypropylene glycol-chain segment polymer of Formula II, below, and mixtures thereof. Without intending to be limited by theory, it is believed that these polypropylene glycols provide a good balance between performance, availability, biodegradability, and cost.

a. Single-polyomomyene Glycol-chain Segment Polymer

Accordingly, a highly preferred single-polypropylene glycol-chain segment polymer has the formula:

$$HO-(C_3H_6O)_aH \qquad \text{(Formula I)},$$

wherein a is a value from about 4 to about 400, preferably from about 20 to about 100, and more preferably from about 20 to about 40.

The single-polypropylene glycol-chain segment polymer useful herein is typically inexpensive, and is readily available from, for example, Sanyo Kaisei (Osaka, Japan), Dow Chemicals (Midland, Mich., USA), Calgene Chemical, Inc. (Skokie, Ill., USA), Arco Chemical Co. (Newton Square Penn., USA), Witco Chemicals Corp. (Greenwich, Conn., USA), and PPG Specialty Chemicals (Gumee, Ill., USA).

Without intending to be limited by theory, it is believed that once it has deposited onto a strand of hair, the shape and relatively small size of the single-polypropylene glycol-chain segment polymer herein allows it to easily penetrate the hair. While useful for both a leave-on and a rinse-off form, a single-polypropylene glycol-chain segment polymer is especially preferred if the hair care composition is to take a leave-on form. Furthermore, the multiple propylene oxide groups attract and maintain a significant amount of water to the hair so as to impart significant moisturization properties. This increased moisturization results in reduced fly-away hair volume, reduced bulk hair volume, and/or increases the manageability of the hair.

b. Multi-polypropylene Glycol-chain Segment Polymer

A highly preferred multi-polypropylene glycol-chain segment polymer has the formula:

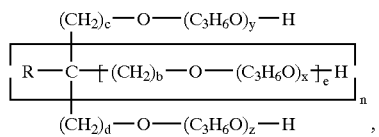
(Formula II)

wherein n is a value from about 0 to about 10, preferably from about 0 to about 7, and more preferably from about 1 to about 4. In Formula II, each R is independently selected from the group consisting of H, and $C_1$–$C_{30}$ alkyl, and preferably each R is independently selected from the group consisting of H, and $C_1$–$C_4$ alkyl. In Formula II, each b is independently a value from about 0 to about 2, preferably from about 0 to about 1, and more preferably b=0. Similarly, c and d are independently a value from about 0 to about 2, preferably from about 0 to about 1. However, the total of b+c+d is at least about 2, preferably the total of b+c+d is from about 2 to about 3. Each e is independently a value of 0 or 1, if n is from about 1 to about 4, then e is preferably equal to 1. Also in Formula II, x, y, and z is independently a value of from about 1 to about 120, preferably from about 7 to about 100, and more preferably from about 7 to about 100, where x+y+z is greater than about 20.

Examples of the multi-polypropylene glycol-chain segment polymer of Formula II which is especially useful herein includes polyoxypropylene glyceryl ether (n=1, R=H, b=0, c and d=1, e=1, and x, y, and z independently indicate the degree of polymerization of their respective polypropylene glycol chain segments; available as New Pol GP4000, from Sanyo Kasei, Osaka, Japan), polypropylene trimethylol propane (n=1, R=$C_2H_6$, b=1, c and d=1, e=1, and x, y, and z independently indicate the degree of polymerization of their respective polypropylene glycol-chain segments), polyoxypropylene sorbitol (n=4, each R=H, b=0, c and d=1, each e=1, and y, z, and each x independently indicate the degree of polymerization of their respective polypropylene glycol-chain segments; available as New Pol SP4000, from Sanyo Kasei, Osaka, Japan), and PPG-10 butanediol (n=0, c and d=2, and y+z=10; available as Probutyl DB-10, from Croda, Inc., of Parsippany, N.J., U.S.A.).

In a preferred embodiment, one or more of the propylene repeating groups in the polypropylene glycol is an isopropyl oxide repeating group. More preferably one or more of the propylene oxide repeating groups of the polypropylene glycol of Formula I and/or the polypropylene glycol of Formula II is an isopropyl oxide repeating group. Even more preferably, substantially all of the propylene oxide repeating groups of the polypropylene glycol of Formula I and/or the polypropylene glycol of Formula II are isopropyl oxide repeating groups. Accordingly, a highly preferred single-polypropylene glycol-chain segment polymer has the formula:

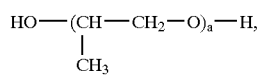
(Formula III)

wherein a is defined as described above for Formula I. Similarly, a highly preferred mult-polypropylene glycol-chain segment polymer has the formula:

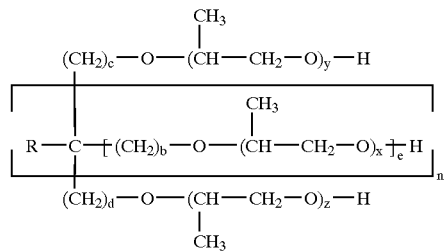
(Formula IV)

wherein n, R, b, c, d, e, x, y, and z are defined as above, for Formula II. It is recognized that the isopropyl oxide repeating groups may also correspond to:

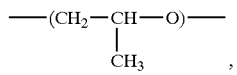

either alone, or in combination with the isomer depicted in Formula IV.

AQUEOUS CARRIER

The compositions of the present invention comprise an aqueous carrier. The level and species of the carrier are selected according to the compatibility with other components, and other desired characteristic of the product.

Carriers useful in the present invention include water and water solutions of lower alkyl alcohols and polyhydric alcohols. Lower alkyl alcohols useful herein are monohydric alcohols having 1 to 6 carbons, more preferably ethanol and isopropanol. Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sultate, sodium hyaluronate, sodium adenosin phosphate, sodium lactate, pyrrolidone carbonate, glucosamine, cyclodextrin, water soluble polyethylene glycols having a molecular weight of up to about 1000 such as those with CTFA names PEG-200, PEG-400, PEG-600, PEG-1000, and mixtures thereof.

Preferably, the aqueous carrier is substantially water, or a water solution of from about 0.5% to about 5% by weight of the composition of, polyhydric alcohol. Deionized water is preferably used. Water from natural sources including mineral cations can also be used, depending on the desired characteristic of the product. Generally, the compositions of the present invention comprise from about 20% to about 99%, preferably from about 40% to about 98%, and more preferably from about 50% to about 98% water.

Commercially available polyhydric alcohols herein include: glycerin with tradenames STAR and SUPEROL available from The Procter & Gamble Company, CRODEROL GA7000 available from Croda Universal Ltd., PRECERIN series available from Unichema, and a same tradename as the chemical name available from NOF; propylene glycol with tradename LEXOL PG865/855 available from Inolex, 1,2-PROPYLENE GLYCOL USP available from BASF; sorbitol with tradenames LIPONIC series available from Lipo, SORBO, ALEX, A-625, and A-641 available from ICI, and UNISWEET 70, UNISWEET CONC available from UPI; dipropylene glycol with the same tradename available from BASF; diglycerin with tradename DIGLYC- EROL available from Solvay GmbH; xylitol with the same tradename available from Kyowa and Eizai; maltitol with tradename MALBIT available from Hayashibara, sodium chondroitin sulfate with the same tradename available from Freeman and Biolberica, and with tradename ATOMERGIC SODIUM CHONDROITIN SULFATE available from Atomergic Chemetals; sodium hyaluronate with tradenames ACTIMOIST available from Active Organics, AVIAN SODIUM HYALURONATE series available from Intergen, HYALURONIC ACID Na available from Ichimamu Pharcos; sodium adenosin phophate with the same tradename available from Asahikasei, Kyowa, and Daiichi Seiyaku; sodium lactate with the same tradename available from Merck, Wako, and Showa Kako, cyclodextin with tradenames CAVITRON available from American Maize, RHODOCAP series available from Rhoneoulenc, and DEX-PEARL available from Tomen; and polyethylene glycols with the tradename CARBOWAX series available from Union Carbide.

The pH of the present composition is preferably from about 4 to about 9, more preferably from about 4.5 to about 7.5. Buffers and other pH adjusting agents can be included to achieve the desirable pH.

SILICONE COMPOUND

The compositions of the present invention may further comprise a silicone compound. The silicone compounds useful herein include volatile soluble or insoluble, or nonvolatile soluble or insoluble silicone conditioning agents. By soluble what is meant is that the silicone compound is miscible with the carrier of the composition so as to form part of the same phase. By insoluble what is meant is that the silicone forms a separate, discontinuous phase from the carrier, such as in the form of an emulsion or a suspension of droplets of the silicone. The silicone compounds herein may be made by any suitable method known in the art, including emulsion polymerization. The silicone compounds may further be incorporated in the present composition in the form of an emulsion, wherein the emulsion is made my mechanical mixing, or in the stage of synthesis through emulsion polymerization, with or without the aid of a surfactant selected from anionic surfactants, nonionic surfactants, cationic surfactants, and mixtures thereof.

The silicone compounds for use herein will preferably have a viscosity of from about 1,000 to about 2,000,000 centistokes at 25° C., more preferably from about 10,000 to about 1,800,000, and even more preferably from about 100,000 to about 1,500,000. The viscosity can be measured by means of a glass capillary viscometer as set forth in Dow Coming Corporate Test Method CTM0004, Jul. 20, 1970. Silicone compound of high molecular weight may be made by emulsion polymerization. Suitable silicone fluids include polyalkyl siloxanes, polyaryl siloxanes, polyalkylaryl siloxanes, polyether siloxane copolymers, and mixtures thereof. Other nonvolatile silicone compounds having hair conditioning properties can also be used.

The silicone compounds herein are preferably used at levels by weight of the composition of from about 0.1% to about 10%, more preferably from about 0.5% to about 3.0%.

The silicone compounds herein also include polyalkyl or polyaryl siloxanes with the following structure (I)

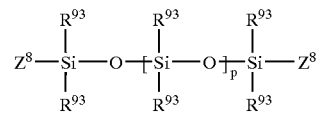

(I)

wherein $R^{93}$ is alkyl or aryl, and x is an integer from about 7 to about 8,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the hair, is compatible with the other components of the composition, is chemically stable under normal use and storage conditions, and is capable of being deposited on and conditions the hair. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their Viscasil® and SF 96 series, and from Dow Coming in their Dow Coming 200 series.

Polyalkylaryl siloxane fluids can also be used and include, for example, polymethylphenylsiloxanes. These siloxanes are available, for example, from the General Electric Company as SF 1075 methyl phenyl fluid or from Dow Coming as 556 Cosmetic Grade Fluid.

Especially preferred, for enhancing the shine characteristics of hair, are highly arylated silicone compounds, such as highly phenylated polyethyl silicone having refractive index of about 1.46 or higher, especially about 1.52 or higher. When these high refractive index silicone compounds are used, they should be mixed with a spreading agent, such as a surfactant or a silicone resin, as described below to decrease the surface tension and enhance the film forming ability of the material.

The silicone compounds that can be used include, for example, a polypropylene oxide modified polydimethylsiloxane although ethylene oxide or mixtures of ethylene oxide and propylene oxide can also be used. The ethylene oxide and polypropylene oxide level should be sufficiently low so as not to interfere with the dispersibility characteristics of the silicone. These material are also known as dimethicone copolyols.

Other silicone compounds include amino substituted materials. Suitable alkylamino substituted silicone compounds include those represented by the following structure (II)

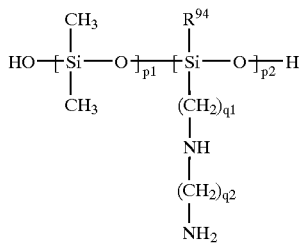

(II)

wherein $R^{94}$ is H, $CH_3$ or OH, $p^1$, $p^2$, $q^1$ and $q^2$ are integers which depend on the molecular weight, the average molecular weight being approximately between 5,000 and 10,000. This polymer is also known as "amodimethicone".

Suitable amino substituted silicone fluids include those represented by the formula (III)

$(R^{97})_aG_{3-a}$—Si—$(OSiG_2)_{p3}$—$(OSiG_b(R^{97})_{2-b})_{p4}$—O—$SiG_{3-a}(R^{97})_a$ (III)

in which G is chosen from the group consisting of hydrogen, phenyl, OH, $C_1$–$C_8$ alkyl and preferably methyl; a denotes 0 or an integer from 1 to 3, and preferably equals 0; b denotes 0 or 1 and preferably equals 1; the sum $p^3+p^4$ is a number from 1 to 2,000 and preferably from 50 to 150, $p^3$ being able to denote a number from 0 to 1,999 and preferably from 49 to 149 and $p^4$ being able to denote an integer from 1 to 2,000 and preferably from 1 to 10; $R^{97}$ is a monovalent radical of formula $C_{q3}H_{2q3}L$ in which $q^3$ is an integer from 2 to 8 and L is chosen from the groups —$N(R^{96})CH_2$—$CH_2$—$N(R^{96})_2$
—$N(R^{96})_2$
—$N(R^{96})_3X'$
—$N(R^{96})CH_2$—$CH_2$—$NR^{96}H_2X'$ in which $R^{96}$ is chosen from the group consisting of hydrogen, phenyl, benzyl, a saturated hydrocarbon radical, preferably an alkyl radical containing from 1 to 20 carbon atoms, and X' denotes a halide ion.

An especially preferred amino substituted silicone corresponding to formula (II) is the polymer known as "trimethylsilylamodimethicone" wherein $R^{94}$ is $CH_3$.

Other amino substituted silicone polymers which can be used are represented by the formula (V):

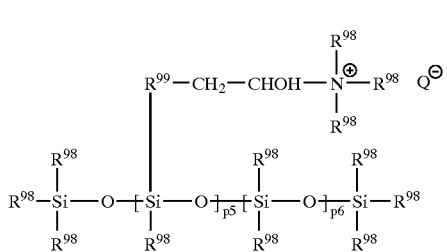

(V)

where $R^{98}$ denotes a monovalent hydrocarbon radical having from 1 to 18 carbon atoms, preferably an alkyl or alkenyl radical such as methyl; $R^{99}$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; $p^5$ denotes an average statistical value from 2 to 20, preferably from 2 to 8; $p^6$ denotes an average statistical value from 20 to 200, and preferably from 20 to 50. A preferred polymer of this class is available from Union Carbide under the name "UCAR SILICONE ALE 56."

References disclosing suitable nonvolatile dispersed silicone compounds include U.S. Pat. No. 2,826,551, to Green; U.S. Pat. No. 3,964,500, to Drakoff, issued Jun. 22, 1976; U.S. Pat. No. 4,364,837, to Pader; and British Patent No. 849,433, to Woolston. "Silicon Compounds" distributed by Petrarch Systems, Inc., 1984, provides an extensive, though not exclusive, listing of suitable silicone compounds.

Another nonvolatile dispersed silicone that can be especially useful is a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. Silicone gums are described by Petrarch, and others including U.S. Pat. No. 4,152,416, to Spitzer et al, issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. The "silicone gums" will typically have a mass molecular weight in excess of about 200,000, generally between about 200,000 and about 1,000,000. Specific examples include polydimethylsiloxane, poly (dimethylsiloxane methylvinylsiloxane) copolymer, poly (dimethylsiloxane diphenylsiloxane methylvinylsiloxane) copolymer and mixtures thereof.

Also useful are silicone resins, which are highly crosslinked polymeric siloxane systems. The crosslinking is introduced through the incorporation of trifunctional and tetra-functional silanes with mono-functional or di-functional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinylchlorosilanes, and tetrachlorosilane, with the methyl substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art. Without being bound by theory, it is believed that the silicone resins can enhance deposition of other silicone compounds on the hair and can enhance the glossiness of hair with high refractive index volumes.

Other useful silicone resins are silicone resin powders such as the material given the CTFA designation polymethylsilsequioxane, which is commercially available as Tospearl™ from Toshiba Silicones.

The method of manufacturing these silicon compounds, can be found in Encyclopedia of Polymer Science and Engineering, Volume 15, Second Edition, pp. 204–308, John Wiley & Sons, Inc., 1989.

Silicone materials and silicone resins in particular, can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the mono-functional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit SiO2. Primes of the unit symbols, e.g., M', D', T', and Q' denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T', and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MO resins wherein the M:Q ratio is from about 0.5:1.0 to about 1.5:1.0 and the average molecular weight of the resin is from about 1000 to about 10,000.

In a preferred embodiment of the present invention, the silicone compound is selected from the group consisting of Dimethicone fluid, Dimethicone gum, Dimethiconol fluid, and mixtures thereof. Particularly suitable silicone compounds herein are non-volatile silicone fluids having a molecular weight of from about 200,000 to about 600,000 such as Dimethicone, and Dimethiconol. These silicone compounds can be incorporated in the composition as silicone oils solutions; the silicone oils being lower silicone oils. Volatile and non-volable silicone oils useful for providing such solutions are cyclic or linear polydimethyl siloxanes. Cyclic polydimethyl siloxanes as know as Cyclomethicones. Preferred silicone oils are Cyclomethicones with about 3–7 silicon atoms having a viscosity of less than about 10 centipoise. Also preferred are linear polydimethylsiloxanes having about 3–9 silicon atoms. Commercially available silicone oils useful as solvents herein are available from Dow Coming as DC344 and 345, and from Union Carbide as Silicone 7202 and 7158, and Stauffer Chemical as SWS-03314.

Commercially available silicone compounds which are useful herein include Dimethicone with tradename DC200 available from Dow Corning Corporation and with tradename CF330M available from General Electric, Dimethicone gum solutions with tradenames SE 30, SE 33, SE 54 and SE 76 available from General Electric, Dimethiconol with tradenames DCQ2-1403 and DCQ2-1401 available from Dow Corning Corporation, and emulsion polymerized Dimethiconol available from Toshiba Silicone as described in GB application 2,303,857.

LOW MELTING POINT OILS

The hair conditioning composition of the present invention may further comprise a low melting point oil, which has a melting point of less than 25° C., and is preferably included in the composition at a level by weight of from about 0.1% to about 5%, more preferably from about 0.2% to about 2%. The low melting point oil herein provides an improved rinse feel by eliminating the ease of rinsing difficulties. It is believed that the poly cc-olefin oil reduces the slicky/slimy feel of other conditioning agents by imparting a draggy feel to the hair when the hair is rinsed. Low melting point oils useful herein include fatty alcohols and their derivatives, fatty acids and their derivatives, hydrocarbons, poly-α olefin oils, and high molecular weight ester oils. The additional oily compounds of this section are to be distinguished from the high melting point compounds described above. Nonlimiting examples of the additional oily compounds are found in International Cosmetic Ingredient Dictionary, Fift Edition, 1993, and CTFA Cosmetic Ingredient Handbook, Second Edition, 1992.

The fatty alcohols useful herein include those having from about 10 to about 30 carbon atoms, preferably from about 12 to about 22 carbon atoms, and more preferably from about 16 to about 22 carbon atoms. These fatty alcohols can be straight or branched chain alcohols and are unsaturated alcohols, preferably unsaturated alcohols. Nonlimiting examples of these compounds include oleyl alcohol, palmitoleic alcohol, linoleyl alcohol, and recinoleyl alcohol.

The fatty acids useful herein include those having from about 10 to about 30 carbon atoms, preferably from about 12 to about 22 carbon atoms, and more preferably from about 16 to about 22 carbon atoms. These fatty acids can be straight or branched chain acids and are unsaturated. Suitable fatty acids include, for example, oleic acid, linoleic acid, linolenic acid, ethyl linolenic acid, ethyl linolenic acid, arachidonic acid, and ricinolic acid.

The fatty acid derivatives and fatty alcohol derivatives are defined herein to include, for example, esters of fatty alcohols, alkoxylated fatty alcohols, alkyl ethers of fatty alcohols, alkyl ethers of alkoxylated fatty alcohols, and bulky ester oils such as pentaerythrtol ester oils, trimethylol ester oils, citrate ester oils, glyceryl ester oils, and mixtures thereof. Nonlimiting examples of fatty acid derivatives and fatty alcohol derivatives, include, for example, methyl linoleate, ethyl linoleate, isopropyl linoleate, isodecyl oleate, isopropyl oleate, ethyl oleate, octyldodecyl oleate, oleyl oleate, decyl oleate, butyl oleate, methyl oleate, octyldodecyl stearate, octyldodecyl isostearate, octyldodecyl isopalmitate, octyl isopelargonate, octyl pelargonate, hexyl isostearate, isopropyl isostearate, isodecyl isononanoate, isopropyl isostearate, ethyl isostearate, methyl isostearate and Oleth-2. Bulky ester oils such as pentaerythritol ester oils, trimethylol ester oils, citrate ester oils and glyceryl ester oils useful herein are those which have a molecular weight of less than about 800, preferably less than about 500.

The hydrocarbons useful herein include straight chain, cyclic, and branched chain hydrocarbons which can be either saturated or unsaturated, so long as they have a melting point of not more than about 25° C. These hydrocarbons have from about 12 to about 40 carbon atoms, preferably from about 12 to about 30 carbon atoms, and preferably from about 12 to about 22 carbon atoms. Also encompassed herein are polymeric hydrocarbons of alkenyl monomers, such as polymers of $C_{2-6}$ alkenyl monomers. These polymers can be straight or branched chain polymers. The straight chain polymers will typically be relatively short in length, having a total number of carbon atoms as described above. The branched chain polymers can have substantially higher chain lengths. The number average molecular weight of such materials can vary widely, but will typically be up to about 500, preferably from about 200 to about 400, and more preferably from about 300 to about 350. Also useful herein are the various grades of mineral oils. Mineral oils are liquid mixtures of hydrocarbons that are obtained from petroleum. Specific examples of suitable hydrocarbon materials include paraffin oil, mineral oil, dodecane, isododecane, hexadecane, isohexadecane, eicosene, isoeicosene, tridecane, tetradecane, polybutene, polylsobutene, and mixtures thereof.

Commercially available fatty alcohols and their derivatives useful herein include: oleyl alcohol with tradename UNJECOL 90BHR available from Shin Nihon Rika, various liquid esters with tradenames SCHERCEMOL series available from Scher, and hexyl isostearate with a tradename HIS and isopropryl isostearate having a tradename ZPIS available from Kokyu Alcohol. Commercially available bulky ester oils useful herein include: trimethylolpropane tricaprylateltricaprate with tradename MOBIL ESTER P43 from Mobil Chemical Co. Commercially available hydrocarbons useful herein include isododecane, isohexadeance, and isoeicosene with tradenames PERMETHYL 99A, PERMETHYL 101A, and PERMETHYL 1082, available from Presperse (South Plainfield N.J., USA), a copolymer of isobutene and normal butene with tradenames INDOPOL H-100 available from Amoco Chemicals (Chicago Ill., USA), mineral oil with tradename BENOL available from witco, and isoparaffin with tradename ISOPAR from Exxon Chemical Co. (Houston Tex., USA).

Poly α-olefin oils useful herein are those derived from 1-alkene monomers having from about 6 to about 16 carbons, preferably from about 6 to about 12 carbons atoms. Nonlimiting examples of 1-alkene monomers useful for preparing the poly α-olefin oils include 1-hexene, 1-octene, 1-decene, 1-dodecene, 1-tetradecene, 1-hexadecene, branched isomers such as 4-methyl-1-pentene, and mixtures thereof. Preferred 1-alkene monomers useful for preparing the poly α-olefin oils are 1-decene, 1-decene, 1-dodecene, 1-tetradecene, 1-hexadecene, and mixtures thereof. Poly α-olefin oils useful herein further have a viscosity of from about 1 to about 35,000 cst, a molecular weight of from about 200 to about 60,000, preferably less than 6,000, and more preferably 800; and a polydispersity of no more than about 3.

Particularly useful poly α-olefin oils herein include polydecenes with tradenames PURESYN 6 having a number average molecular weight of about 500, PURESYN 100 having a number average molecular weight of about 3000 and PURESYN 300 having a number average molecular weight of about 6000 available from Mobil Chemical Co.

High molecular weight ester oils useful herein include pentaerythritol ester oils, trimethylol ester oils, citrate ester oils, glyceryl ester oils, and mixtures thereof. The high molecular weight ester oils herein are "Water-insoluble". As used herein, the term "water-insoluble" means the compound is substantially not soluble in water at 25° C.; when the compound is mixed with water at a concentration by weight of above 1.0%, preferably at above 0.5%, the compound is temporarily dispersed to form an unstable colloid in water, then is quickly separated from water into two phases.

Pentaerythritol ester oils useful herein are those having the following formula:

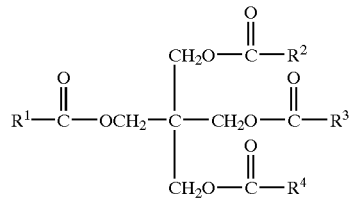

wherein $R^1$, $R^2$, $R^3$, and $R^4$, independently, are branched, straight, saturated, or unsaturated alkyl, aryl, and alkylaryl groups having from 1 to about 30 carbons. Preferably, $R^1$, $R^2$, $R^3$, and $R^4$, independently, are branched, straight, saturated, or unsaturated alkyl groups having from about 8 to about 22 carbons. More preferably, $R^1$, $R^2$, $R^3$ and $R^4$ are defined so that the molecular weight of the compound is from about 800 to about 1200.

Trimethylol ester oils useful herein are those having the following formula:

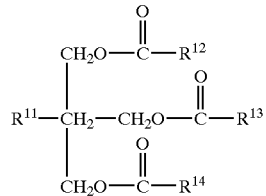

wherein $R^{11}$ is an alkyl group having from 1 to about 30 carbons, and $R^{12}$, $R^{13}$, and $R^{14}$, independently, are branched, straight, saturated, or unsaturated alkyl, aryl, and alkylaryl groups having from 1 to about 30 carbons. Preferably, $R^{11}$ is ethyl and $R^{12}$, $R^{13}$, and $R^{14}$, independently, are branched, straight, saturated, or unsaturated alkyl groups having from 8 to about 22 carbons. More preferably, $R^{11}$, $R^{12}$, $R^{13}$ and $R^{14}$ are defined so that the molecular weight of the compound is from about 800 to about 1200.

Particularly useful pentaerythritol ester oils and trimethylol ester oils herein include pentaerythritol tetraisostearate, pentaerythritol tetraoleate, trimethylolpropane triisostearate, trimethylolpropane trioleate, and mixtures thereof. Such compounds are available from Kokyo Alcohol with tradenames KAKPTI, KAKTTI, and Shin-nihon Rika with tradenames PTO, ENUJERUBU TP3SO.

Citrate ester oils useful herein are those having a molecular weight of at least about 500 having the following formula:

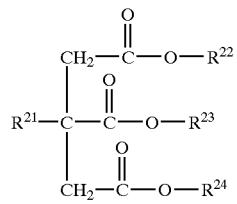

wherein $R^{21}$ is OH or $CH_3COO$, and $R^{22}$, $R^{23}$, and $R^{24}$, independently, are branched, straight, saturated, or unsaturated alkyl, aryl, and alkylaryl groups having from 1 to about 30 carbons. Preferably, $R^{21}$ is OH, and $R^{22}$, $R^{23}$, and $R^{24}$, independently, are branched, straight, saturated, or unsaturated alkyl, aryl, and alkylaryl groups having from 8 to about 22 carbons. More preferably, $R^{21}$, $R^{22}$, $R^{23}$ and $R^{24}$ are defined so that the molecular weight of the compound is at least about 800.

Particularly useful citrate ester oils herein include triisocetyl citrate with tradename CITMOL 316 available from Bemel, triisostearyl citrate with tradename PELEMOL TISC available from Phoenix, and trioctyldodecyl citrate with tradename CITMOL 320 available from Bemel.

Glyceryl ester oils useful herein are those having a molecular weight of at least about 400 and having the following formula:

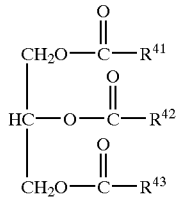

wherein $R^{41}$, $R^{42}$, and $R^{43}$, independently, are branched, straight, saturated, or unsaturated alkyl, aryl, and alkylaryl groups having from 1 to about 30 carbons. Preferably, $R^{41}$, $R^{42}$, and $R^{43}$, independently, are branched, straight, saturated, or unsaturated alkyl, aryl, and alkylaryl groups having from 8 to about 22 carbons. More preferably, $R^{41}$, $R^{42}$, and $R^{43}$ are defined so that the molecular weight of the compound is at least about 500.

Particularly useful glyceryl ester oils herein include triisostearin with tradename SUN ESPOL G-318 available from Taiyo Kagaku, triolein with tradename CITHROL GTO available from Croda Surfactants Ltd., trilinolein with tradename EFADERMA available from Vevy, or tradename EFA-GLYCERIDES from Brooks.

AMPHOTERIC CONDITIONING POLYMER

The compositions of the present invention may further comprise an amphoteric conditioning polymer. The amphoteric conditioning polymers herein are those compatible with the carboxylic acid/carboxylate copolymers and which provide conditioning benefit to the hair. Although some of the amphoteric conditioning polymers herein may have some hair holding or hair fixative properties, such hair holding or hair fixative properties are not a requirement for the amphoteric conditioning polymers herein. The amphoteric conditioning polymers useful herein are those including at least one cationic monomer and at least one anionic monomer, the cationic monomer being quaternary ammonium, preferably dialkyl diallyl ammonium chloride or carboxylamidoalkyl trialkyl ammonium chloride; and the anionic monomer being carboxylic acid. The amphoteric conditioning polymers herein may include nonionic monomers such as acrylamine, methacrylate, or ethacrylate. Further, the amphoteric conditioning polymers useful herein do not contain betanized monomers.

The composition of the present invention preferably comprises the amphoteric conditioning polymer at a level by weight of from about 0.05% to about 5%, more preferably from about 0.1% to about 2%.

Useful herein are polymers with the CTFA name Polyquaternium 22, Polyquaternium 39, and Polyquaternium 47. Such polymers are, for example, copolymers consisting of dimethyldiallyl ammonium chloride and acrylic acid, terpolymers consisting of dimethyldiallyl ammonium chloride and acrylamide, and terpolymers consisting of acrylic acid methacrylamidopropyl trimethylammonium chloride and methyl acrylate such as those of the following formula wherein the ratio of $n^6:n^7:n^8$ is 45:45:10:

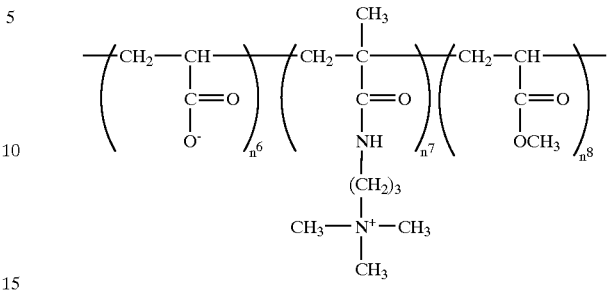

Highly preferred commercially available amphoteric conditioning polymers herein include Polyquaternium 22 with tradenames MERQUAT 280, MERQUAT 295, Polyquaternium 39 with tradenames MERQUAT PLUS 3330, MERQUAT PLUS 3331, and Polyquaternium 47 with tradenames MERQUAT 2001, MERQUAT 2001N, all available from Calgon Corporation.

Also useful herein are polymers resulting from the copolymerisation of a vinyl monomer carrying at least one carboxyl group, such as acrylic acid, methacrylic acid, maleic acid, itaconic acid, fumaric acid, crotonic acid, or alphachloroacrylic acid, and a basic monomer which is a substituted vinyl compound containing at least one basic nitrogen atom, such as dialkylaminoalkyl methacrylates and acrylates and dialkylaminoalkylmethacrylamides and acrylamides.

Also useful herein are polymers containing units derived from:
  i) at least one monomer chosen from amongst acrylamides or methacrylamides substituted on the nitrogen by an alkyl radical,
  ii) at least one acid comonomer containing one or more reactive carboxyl groups, and
  iii) at least one basic comonomer, such as esters, with primary, secondary and tertiary amine substituents and quaternary ammonium substituents, of acrylic and methacrylic acids, and the product resulting from the quaternisation of dimethylaminoethyl methacrylate with dimethyl or diethyl sulfate.

The N-substituted acrylamides or methacrylamides which are most particularly preferred are the groups in which the alkyl radicals contain from 2 to 12 carbon atoms, especially N-ethylacrylamide, N-tert.-butylacrylamide, N-tert.-octylacrylamide, N-octytacrylamide, N-decylacrylamide and N-dodecylacrylamide and also the corresponding methacrylamides. The acid comonomers are chosen more particularly from amongst acrylic, methacrylic, crotonic, itaconic, maleic and fumaric acids and also the alkyl monoesters of maleic acid or fumaric acid in which alkyl has 1 to 4 carbon atoms.

The preferred basic comonomers are aminoethyl, butylaminoethyl, N,N'-dimethylaminoethyl and N-tert.-butylaminoethyl methacrylates.

Commercially available amphoteric conditioning polymers herein include octylacrylamine/acrylates/butylaminoethyl methoacrylate copolymers with the tradenames AMPHOMER, AMPHOMER SH701, AMPHOMER 28-4910, AMPHOMER LV71, and AMPHOMER LV47 supplied by National Starch & Chemical.

ADDITIONAL VISCOSITY MODIFIER

The compositions of the present invention may further comprise an additional viscosity modifier. The additional viscosity modifiers herein are water soluble or water miscible polymers, have the ability to increase the viscosity of the composition, and are compatible with the carboxylic acid/carboxylate copolymers. The additional viscosity modifier is selected so that the composition of the present composition has a suitable viscosity, preferably from about 1,000 cps to about 100,000 cps, more preferably from about 2,000 cps to about 50,000 cps. If such a viscosity is achieved without the additional viscosity modifier, the additional viscosity modifier may not be necessary. The viscosity herein can be suitably measured by Brookfield RVT at 20 rpm at 20° C. using either spindle #4, 5, 6 or 7 depending on the viscosity and the characteristic of the composition. The additional viscosity modifiers herein are preferably used at levels by weight of the composition of from about 0.01% to about 5%, more preferably from about 0.05% to about 2%.

Additional viscosity modifiers useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carragheenin, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Polyethylene glycols having a molecular weight of more than about 1000 are useful herein. Useful are those having the following general formula:

H(OCH$_2$CH)$_{x3}$—OH wherein x3 has an average value of from about 1500 to about 25,000, preferably from about 2500 to about 20,000, and more preferably from about 3500 to about 15,000. Polyethylene glycol polymers useful herein are PEG-2M wherein x3 has an average value of about 2,000 (PEG-2M is also known as Polyox WSR® N-10, which is available from Union Carbide and as PEG-2,000); PEG-5M wherein x3 is has an average value of about 5,000 (PEG-5M is also known as Polyox WSR N-35 and Polyox WSR® N-80, both available from Union Carbide and as PEG-5,000 and Polyethylene Glycol 300,000); PEG-7M wherein x3 has an average value of about 7,000 (PEG-7M is also known as Polyox WSR® N-750 available from Union Carbide); PEG-9M wherein x3 has an average value of about 9,000 (PEG 9-M is also known as Polyox WSR® N-3333 available from Union Carbide); and PEG-14 M wherein x3 has an average value of about 14,000 (PEG-14M is also known as Polyox WSR® N-3000 available from Union Carbide).

Commercially available additional viscosity modifiers highly useful herein include Carbomers with tradenames Carbopol 934, Carbopol 940, Carbopol 950, Carbopol 980, and Carbopol 981, all available from B. F. Goodrich Company, acrylates/steareth-20 methacrylate copolymer with tradename ACRYSOL 22 available from Rohm and Hass, nonoxynyl hydroxyethylcellulose with tradename AMERCELL POLYMER HM-1500 available from Amerchol, methylcellulose with tradename BENECEL, hydroxyethyl cellulose with tradename NATROSOL, hydroxypropyl cellulose with tradename KLUCEL, cetyl hydroxyethyl cellulose with tradename POLYSURF 67, all supplied by Herculus, ethylene oxide and/or propylene oxide based polymers with tradenames CARBOWAX PEGs, POLYOX WASRs, and UCON FLUIDS, all supplied by Amerchol.

VISIBLE PARTICLE

The compositions of the present invention may further comprise a visible particle. By definition, a visible particle is a particle which can be distinctively detected as an individual particle by the naked eye when comprised in the present composition, and which is stable in the present composition. The visible particle can be of any size, shape, or color, according to the desired characteristic of the product, so long as it is distinctively detected asian individual particle by the naked eye. Generally, the visible particle has an average diameter of from about 50 μm to about 3000 μm, preferably from about 100 μm to about 1000 μm, more preferably from about 300 μm to about 1000 μm. By stable, it is meant that the visible particles are not disintegrated, agglomerated, or separated under normal shelf conditions. In one preferred embodiment of the present invention, the composition is substantially transparent. In such an embodiment, the visible particles provide a highly suitable aesthetic benefit. What is generally meant by transparent, is that a black substance having the size of a 1 cm×1cm square can be detected by the naked eye through 1 cm thickness of the present composition.

The visible particles herein are used at levels of from about 0.01% to about 5% by weight of the composition.

The visible particle herein comprises a structural material and preferably an encompassed material.

The structural material provides a certain strength to the visible particle so that they retain their distinctively detectable structure in the present composition under normal shelf conditions. In one preferred embodiment, the structural material further can be broken and disintegrated with very little shear on the hand with the fingers upon use.

Visible particles useful herein include capsules, shelled particles, beads, pellets, droplets, pills, caplets, tablets, grains, flakes, powders and granules. The visible particles can be solid or liquid, filled or un-filled, so long as they are stable in the present composition. The structural material used for making the visible particles varies depending on the compatibility with other components, as well as material, if any, to be encompassed in the visible particles. Exemplary materials for making the visible particles herein include: polysaccharid and saccharide derivatives such as crystalline cellulose, cellulose acetate, cellulose acetate butyrate, cellulose acetate phthalate, cellulose nitrate, ethylcellulose, hydroxypropylcellulose, hydroxypropylmethylcellulose, hydroxypropylmethylcellulose phthalate, methyl cellulose, sodium carboxymethylcellulose, gum acacia (gum arabic), agar, agarose, maltodextrin, sodium alginate, calcium alginate, dextran, starch, galactose, glucosamine, cyclodextrin, chitin, amylose, amylopectin, glycogen, laminaran, lichenan, curdlan, inulin, levan, pectin, mannan, xylan, alginic acid, arabic acid, glucommannan, agarose, agaropectin, prophyran, carrageenen, fucoidan, glycosaminoglycan, hyaluronic acid, chondroitin, peptidoglycan, lipopolysaccharide, guar gum, starch, and starch derivatives; oligosaccharides such as sucrose, lactose, maltose, uronic acid, muramic acid, celloblose, isomaltose, planteose, melezitose, gentianose, maltotriose, stachyose, glucoside and polyglucoside; monosaccharides such as glucose, fructose, and mannose; synthetic polymers such as acrylic polymers and copolymers including polyacrylamide, poly(alkyl cyanoacrylate), and poly(ethylenevinyl acetate), and carboxyvinyl polymer, polyamide, poly(methyl vinyl ether-maleic anhydride), poly(adipyl-L-lysine), polycarbonate, polyterephthalamide, polyvinyl acetate phthalate, poly(terephthaloyl-L-lysine), polyarylsulfone, poly(methylmethacrylate), poly(ε-caprolactone), polyvinylpyrrolidone, polydimethylsiloxane, polyoxyethylene, polyester, polyglycolic acid, polylactic acid, polyglutamic acid, polylysine, polystyrene, poly(styrene-acrylonitrile), polyimide, and poly(vinyl alcohol); and other material such as fat, fatty acid, fatty alcohol, milk solids, molasses, gelatin, gluten, albumin, shellac, caseinate, bees wax, camauba wax, spermaceti wax, hydrogenated tallow, glycerol monopalmitate, glycerol dipalmitate, hydrogenated castor oil, glycerol monostearate, glycerol distearate, glycerol tristearate, 12-hydroxystearyl alcohol, protein, and protein derivatives; and mixtures thereof. Components herein may be described in other sections as useful components for the present composition. The components herein, however, are substantially used to make the structure of the visible particles, and are not dissolved or dispersed in the bulk of the present composition under normal shelf conditions.

Highly preferable structural material herein comprises components selected from the group consisting of polysaccharides and their derivatives, saccharides and their derivatives, oligosaccharides, monosaccharides, and mixtures thereof, still preferably, components from the above mentioned group wherein components having various water solubility are selected. In a particularly preferred embodiment, the structural material is made of components selected from the group consisting of cellulose, cellulose derivatives, saccharides, and mixtures thereof.

The visible particle herein may encompass, contain, or be filled with an encompassed material. Such encompassed material can be water soluble or water insoluble, and comprise components such as: vitamins, amino acids, proteins and protein derivatives, herbal extracts, pigments, dyes, antimicrobial agents, chelating agents, UV absorbers, optical brighteners, silicone compounds, perfumes, humectants which are generally water soluble, additional conditioning agents which are generally water insoluble, and mixtures thereof. In one embodiment, water soluble components are preferred encompassed material. In another embodiment, components selected from the group consisting of vitamins, amino acids, proteins, protein derivatives, herbal extracts, and mixtures thereof are preferred encompassed material. In yet another embodiment, components selected from the group consisting of vitamin E, pantothenyl ethyl ether, panthenol, Polygonum multiflori extracts, and mixtures thereof are preferred encompassed material.

Vitamins and amino acids useful as encompassed material herein include: water soluble vitamins such as vitamin B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

Pigments useful as encompassed material herein include inorganic, nitroso, monoazo, disazo, carotenoid, triphenyl methan, triaryl methane, xanthene, quinoline, oxazine, azine, anthraquinone, indigoid, thionindigoid, quinacridone, phthalocianine, botanical, natural colors, including: water soluble components such as those having C. I. Names: Acid Red 18, 26, 27,33, 51, 52, 87, 88, 92, 94, 95, Acid Yellow 1, 3, 11, 23, 36, 40, 73, Food Yellow 3, Food Green 3, Food blue 2, Food Red 1, 6, Acid Blue 5, 9, 74, Pigment Red 57-1, 53(Na), Basic Violet 10, Solvent Red 49, Acid orange 7, 20, 24, Acid Green 1, 3, 5, 25, Solvent Green 7, Acid Violet 9, 43; water insoluble components such as those having C. I. Names: Pigment Red 53(Ba), 49(Na), 49(Ca), 49(Ba), 49(Sr), 57, Solvent Red 23, 24, 43, 48, 72, 73, Solvent Orange 2, 7, Pigment Red 4, 24, 48, 63(Ca) 3, 64, Vat Red 1, Vat blue 1, 6, Pigment Orange 1, 5, 13, Solvent Yellow 5, 6, 33, Pigment Yellow 1, 12, Solvent Green 3, Solvent Violet 13, Solvent Blue 63, Pigment Blue 15, titanium dioxides, chlorophyllin copper complex, ultramarines, aluminum powder, bentonite, calcium carbonate, barium sulfate, bismuthine, calcium sulfate, carbon black, bone black, chromic acid, cobalt blue, gold, ferric oxides, hydrated ferric oxide, ferric ferrocyanide, magnesium carbonate, manganous phosphate, silver, and zinc oxides.

Antimicrobial agents useful as encompassed material include those useful as cosmetic biocides and antidandruff agents including: water soluble components such as piroctone olamine, water insoluble components such as 3,4,4'-trichlorocarbanilide (trichlosan), tridocarban and zinc pyrithione.

Chelating agents useful as encompassed material include: 2,2'-dipyridylamine; 1,10phenanthroline {o-phenanthroline}; di-2-pyridyl ketone; 2,3-bis(2-pyridyl) pyrazine; 2,3-bis(2-pyridyl)-5,6-dihydropyrazine; 1,1'-carbonyldiimidazole; 2,4-bis(5,6-diphenyl-1,2,4-triazine-3-yl)pyridine; 2,4,6-tri(2-pyridyl)-1,3,5-triazine; 4,4'-dimethyl-2,2'-dipyridyl; 2,2'-biquinoline; di-2-pyridyl glyoxal {2,2'-pyridil}; 2-(2-pyridyl)benzimidazole; 2,2'-bipyrazine; 3-(2-pyridyl)-5,6-diphenyl-1,2,4-triazine; 3-(4-phenyl-2-pyridyl)-5-phenyl-1,2,4-triazine; 3-(4-phenyl-2-pyridyl)-5,6-diphenyl-1,2,4-triazine; 2,3,5,6-tetrakis-(2'-pyridyl)pyrazine; 2,6-pyridinedicarboxylic acid; 2,4,5-trihydroxypyrimidine; phenyl 2-pyridyl ketoxime; 3-amino-5,6-dimethyl-1,2,4-triazine; 6-hydroxy-2-phenyl-3(2H)-pyridazinone; 2,4-pteridinediol {lumazine}; 2,2-'dipyridyl; and 2,3-dihydroxypyridine.

Useful silicone compounds, humectants, additional conditioning agents, UV absorbers, optical brighteners, and herbal extracts for encompassed material are the same as those exemplified in other portions of the specification. The components herein, however, are substantially retained within the breakable visible particles, and are substantially not dissolved in the bulk of the present composition under normal shelf conditions.

Particularly useful commercially available visible particles herein are those with tradenames Unisphere and Unicerin available from Induchem AG (Switzerland), and Confetti Dermal Essentials available from United-Guardian Inc. (NY, USA). Unisphere and Unicerin particles are made of microcrystalline cellulose, hydroxypropyl cellulose, lactose, vitamins, pigments, and proteins. Upon use, the Unisphere and Unicerin particles can be disintegrated with very little shear on the hand with the fingers with practically no resistance, and readily dissolve in the composition.

HERBAL EXTRACT

The compositions of the present invention may further comprise herbal extracts. Herbal extracts useful herein include those which are water soluble and those which are water insoluble. Useful herbal extracts herein include: Polygonum multiflori Extract, Houttuynia cordate extract, Phellodendron Bark extract, melilot extract, white dead nettle extract, licorice root extract, herbaceous peony extract, soapwort extract, dishcloth gourd extract, cinchona extract, creeping saxifrage extract, Sophora angustifolia extract, candock extract, common fennel extract, primrose extract, rose extract, Rehmannia glutinosa extract, lemon extract, shikon extract, alloe extract, iris bulb extract, eucalyptus extract, field horsetail extract, sage extract, thyme extract, tea extract, laver extract, cucumber extract, clove extract, raspberry extract, melissa extract, ginseng extract, carrot extract, horse chestnut extract, peach extract, peach leaf extract, mulberry extract, cornflower extract, hamamelis extract, placenta extract, thymus extract, silk extract, algae extract, althea extract, angelica dahurica extract, apple extract, apricot kernel extract, arnica extract, Artemisia capillaris extract, astragal extract, balm mint extract, perilla extract, birch bark extract, bitter orange peel extract, Thea sinensis extract, burdock root extract, burnet extract, butcherbroom extract, Stephania cepharantha extract, matricaria extract, chrysanthemum flower extract, citrus unshiu peel extract, cnidium extract, coix seed extract, coltsfoot extract, cornfrey leaf extract, crataegus extract, evening primrose oil, gambir extract, ganoderma extract, gardenia extract, gentian extract, geranium extract, ginkgo extract, grape leaf extract, crataegus extract, henna extract, honeysuckle extract, honeysuckle flower extract, hoelen extract, hops extract, horsetail extract, hydrangea extract, hypericum extract, isodonis extract, ivy extract, Japanese angelica extract, Japanese coptis extract, juniper extract, jujube extract, lady's mantle extract, lavender extract, lettuce extract, licorice extract, linden extract, lithospermum extract, loquat extract, luffa extract, malloti extract, mallow extract, calendula extract, moutan bark extract, mistletoe extract, mukurossi extract, mugwort extract, mulberry root extract, nettle extract, nutmeg extract, orange extract, parsely extract, hydrolyzed conchiorin protein, peony root extract, peppermint extract, philodendron extract, pine cone extract, platycodon extract, polygonatum extract, rehmannia extract, rice bran extract, rhubarb extract, rose fruit extract, rosemary extract, royal jelly extract, safflower extract, saffron crocus extract, sambucus extract, saponaria extract, Sasa albo marginata extract, Saxifraga stolonifera extract, scutellaria root extract, Cortinellus shiltake extract, lithospermum extract, sophora extract, laurel extract, calamus root extract, swertia extract, thyme extract, linden extract, tomato extract, turmeric extract, uncaria extract, watercress extract, logwood extract, grape extract, white lily extract, rose hips extract, wild thyme extract, witch hazel extract, yarrow extract, yeast extract, yucca extract, zanthoxylum extract, and mixtures thereof.

Commercially available herbal extracts useful herein include Polygonum multiflori extracts which are water soluble, and available from Institute of Occupational Medicine, CAPM, China National Light Industry, and Mamuzen, and other herbal extracts listed above available from Maruzen.

UV ABSORBER

The compositions of the present invention may further comprise a UV (ultraviolet) absorber. UV absorbers are particularly useful for compositions of the present invention which are substantially transparent The UV absorbers herein are preferably used at levels by weight of the composition of from about 0.01% to about 10%.

UV absorbers useful herein can be water soluble or water insoluble, including: p-aminobenzoic acid, its salts and its derivatives (ethyl, isobutyl, glyceryl esters; p-dimethylaminobenzoic acid); anhranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); cinnamic acid derivatives (menthyl and benzyl esters, -phenyl cinnamonitrile; butyl cinnamoyl pyruvate; trihydroxycinnamic acid derivatives (esculetin, methylesculetin, daphnetin, and the glucosides, esculin and daphnin); dibenzalacetone and benzalacetophenone; naphtholsulfonates (sodium salts of 2-naphthol-3,6-disulfonic and of 2-naphthol-6,8-disulfonic acids); dihydroxynaphthoic acid and its sals; o- and p-Hydroxybiphenyldisulfonates; quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbityl) (6-propyl piperonyl) ether; hydroquinone; benzophenones (oxybenzene, sulisobenzone, dioxybenzone, benzoresorcinol, 2,2',4,4'-Tetrahydroxybenzophenone, 2,2'-Dihydroxy-4,4'-dimethoxybenzophenone, octabenzone); 4-isopropyldibenzoylmethane; butylmethoxydibenzoylmethane; etocrylene; and 4-isopropyl-di-benzoylmethane. Of these, 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone ethyl 4-[bis(hydroxypropyl)] aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl p-dimethylamino-benzoate, 2-phenylbenzimidazole-5-sulfonic acid, 2-(p-dimethylaminophenyl)-5-sulfonicbenzoxazoic acid and mixtures thereof. Preferred sunscreens useful in the compositions of the present invention are 2-ethylhexyl p-methoxycinnamate, butylmethoxydibenzoylmethane, 2-hydroxy-4-methoxybenzophenone, octyldimethyl p-aminobenzoic acid and mixtures thereof.

HIGH MELTING POINT COMPOUND

The compositions of the present invention may further comprise a high melting point compound. The high melting point compound useful herein have a melting point of at least about 25° C. selected from the group consisting of fatty alcohols, fatty acids, fatty alcohol derivatives, fatty acid derivatives, hydrocarbons, steroids, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than about 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

It is believed that these high melting point compounds cover the hair surface and reduce friction, thereby resulting in providing smooth feel on the hair and ease of combing.

The fatty alcohols useful herein are those having from about 14 to about 30 carbon atoms, preferably from about 16 to about 22 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids can be straight or branched chain adds and can be saturated or unsaturated. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$–$C_{30}$ alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

Hydrocarbons useful herein include compounds having at least about 20 carbons.

Steroids useful herein include compounds such as cholesterol.

High melting point compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsabilty from the hair when the consumer rinses off the composition.

Commercially available high melting point compounds useful herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan), various fatty acids having tradenames NEO-FAT available from Akzo (Chicago Ill., USA), HYSTRENE available from Witco Corp. (Dublin Ohio, USA), and DERMA available from Vevy (Genova, Italy); and cholesterol having tradename NIKKOL AGUASOME LA available from Nikko.

Other Additional Components

The compositions of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; hair-fixative polymers such as amphoteric fixative polymers, cationic fixative polymers, anionic fixative polymers, nonionic fixative polymers, and silicone grafted copolymers; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents such as the thioglycolates; perfumes; and sequestering agents, such as disodium ethylenediamine tetra-acetate; ultraviolet and infrared screening and absorbing agents such as octyl salicylate, antidandruff agents such as zinc pyrithione; and optical brighteners, for example polystyrylsilbenes, triazinstilbenes, hydroxycoumarins, aminocoumarins, triazoles, pyrazolines, oxazoles, pyrenes, porphyrins, imidazoles, and mixtures thereof.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below.

The compositions of the present invention are suitable for making products in the form of emulsion, cream, gel, spray or, mousse, and are particularly used for leaven products in the form of gel. The products can be used on wet hair or dried hair.

| Components | Compositions | | | | | |
|---|---|---|---|---|---|---|
| | Ex. 1 | Ex. 2 | Ex. 3 | Ex. 4 | Ex. 5 | Ex. 6 |
| Carboxylic acid/carboxylate copolymer 1 *1 | 0.35 | 0.5 | | | 1.2 | 0.4 |
| Carboxylic acid/carboxylate copolymer 2 *2 | | | 0.4 | | | 0.5 |
| Polyethylene Glycol 200 *3 | 2.0 | | 1.0 | | | 2.0 |
| Polypropylene Glycol 1000 *4 | | 2.5 | | | | 1.8 |
| Polypropylene Glycol 2000 *5 | 2.0 | | 1.5 | | 2.25 | |
| Polypropylene Glycol 4000 *6 | | | | 1.2 | | |
| Triethanolamine *9 | 0.5 | 0.6 | 0.5 | 0.9 | 0.5 | 0.7 |
| Polyquaternium 39 *10 | 0.2 | | | 0.1 | | 0.5 |
| Polyquaternium 47 *11 | | | 0.1 | | 0.2 | |
| Carbomer 1 *12 | 0.1 | | 0.2 | | | 0.2 |
| Carbomer 2 *13 | | | | | 0.2 | |
| Dimethicone and Dimethiconol *14 | | 1.0 | 1.0 | | | 1.5 |
| Cyclomethicone/ Dimethicone *15 | | 0.5 | | | 0.25 | |
| Dimethicone *16 | | | | 1.0 | | |
| Hexylene Glycol *17 | | 1.0 | | | 2.0 | |
| Polygonum multiflori extract *18 | 0.1 | | | | | |
| Vitamin E *19 | | | | 0.1 | | |
| Panthenol *20 | | | | 0.1 | | 0.1 |
| Visible particles 1 *21 | 0.1 | | | 0.2 | | |
| Visible particles 2 *22 | | 0.1 | | | 0.2 | |
| Methyl Paraben | 0.2 | 0.2 | 0.2 | 0.2 | 0.2 | 0.2 |
| Phenoxyethanol | 0.3 | 0.3 | 0.3 | 0.3 | 0.3 | 0.3 |
| Disodium EDTA | 0.1 | 0.1 | 0.1 | 0.1 | 0.1 | 0.1 |
| Perfume solution | 0.1 | 0.1 | 0.1 | 0.1 | 0.1 | 0.1 |
| Deionized Water | q.s. to 100% | | | | | |

| Components | Ex. 7 | Ex. 8 | Ex. 9 | Ex. 10 | Ex. 11 | Ex. 12 |
|---|---|---|---|---|---|---|
| Carboxylic acid/carboxylate copolymer 1 *1 | 0.35 | 0.35 | 0.5 | | 1.0 | |
| Carboxylic acid/carboxylate copolymer 2 *2 | | | | 0.5 | | 1.0 |
| Polyethylene Glycol 200 *3 | 2.0 | 2.0 | | | 1.0 | |
| Polypropylene Glycol 1000 *4 | | | | 3.0 | | 1.8 |
| Polypropylene Glycol 2000 *5 | | | 1.5 | | | |
| Polypropylene Glycol 4000 *6 | | | | | 1.0 | |
| Oleth-5 *7 | 2.0 | | | | | |
| Steareth-4 *8 | | 2.0 | | | | |
| Triethanolamine *9 | 0.5 | 0.5 | 0.6 | 0.6 | 0.8 | 0.8 |
| Polyquaternium 39 *10 | 0.2 | 0.2 | 0.2 | | | 0.5 |
| Polyquaternium 47 *11 | | | | 0.2 | | |
| Carbomer 1 *12 | 0.1 | 0.1 | | | | |
| Carbomer 2 *13 | | | | | | |
| Dimethicone and Dimethiconol *14 | 1.0 | 1.0 | | | | |
| Cyclomethicone/ Dimethicone *15 | | | | 0.2 | | |
| Dimethicone *16 | | | | | 0.1 | |
| Hexylene Glycol *17 | | | | 2.0 | | |
| Polygonum multiflori extract *18 | 0.1 | 0.1 | | 0.2 | | 0.2 |
| Visible particles 1 *21 | 0.1 | 0.1 | | | | |
| Cetyl hydroxyethylcellulose *23 | | | | | | 0.2 |
| Polyquaternium 22 *25 | | | | | 0.1 | |
| Oleyl Alcohol *26 | | | 2.0 | | 1.0 | |
| Pentaerythritol Tetraisostearate *27 | | | | 0.5 | | 0.1 |
| Ginseng *29 | | | | | 0.2 | |
| Methyl Paraben | 0.2 | 0.2 | 0.2 | 0.2 | 0.2 | 0.2 |
| Phenoxyethanol | 0.3 | 0.3 | 0.1 | 0.1 | 0.1 | 0.1 |
| Disodium EDTA | 0.1 | 0.1 | 0.1 | 0.1 | 0.1 | 0.1 |
| Perfume solution | 0.1 | 0.1 | 0.1 | 0.1 | 0.1 | 0.1 |
| Deionized Water | q.s. to 100% | | | | | |

| Components | Ex. 13 | Ex. 14 | Ex. 15 | Ex. 16 |
|---|---|---|---|---|
| Carboxylic acid/carboxylate copolymer 1 *1 | | | 0.5 | 0.5 |
| Carboxylic acid/carboxylate copolymer 2 *2 | 0.3 | 0.3 | | |
| Polypropylene Glycol 2000 *5 | 2.2 | | | |
| Polypropylene Glycol 4000 *6 | | 1.6 | | |
| Oleth-5 *7 | | | 1.5 | |
| Steareth-4 *8 | | | | 1.5 |
| Triethanolamine *9 | 0.3 | 0.6 | 0.6 | 0.6 |
| Polyquaternium 47 *11 | | 2.0 | | |
| Dimethicone/ Dimethiconol *14 | 2.0 | | | |
| Hydroxyethylcellulose *24 | 0.1 | | | |
| Polyquaternium 39 *25 | 1.0 | | 0.2 | 0.2 |
| Oleyl Alcohol *26 | 0.5 | | 2.0 | 2.0 |
| Pentaerythritol Tetraisostearate *27 | | 0.2 | | |
| Aloe Extract *28 | | 1.0 | | |
| Methyl Paraben | 0.2 | 0.2 | 0.2 | 0.2 |
| Phenoxyethanol | 0.1 | 0.1 | 0.1 | 0.1 |
| Disodium EDTA | 0.1 | 0.1 | 0.1 | 0.1 |
| Perfume solution | 0.1 | 0.1 | 0.1 | 0.1 |
| Deionized Water | q.s. to 100% | | | |

Definitions of Components
*1 Carboxylic acid/carboxylate copolymer-1: PEMULEN TR-1 available from B. F. Goodrich
*2 Carboxylic acid/carboxylate copolymer-2: PEMULEN TR-2 available from B. F. Goodrich
*3 Polyethylene Glycol 200: Carbowax PEG200 available from Union Carbide
*4 Polypropylene Glycol 1000: Newpol PP1000 available from Sanyo Kasei
*5 Polypropylene Glycol 2000: Newpol PP2000 available from Sanyo Kasei
*6 Polypropylene Glycol 4000: Newpol PP4000 available from Sanyo Kasei
*7 Oleth-5: Volpo-5 Croda
*8 Steareth-4: Nikko Chemical
*9 Triethanolamine: Triethanolamine available from Nippon Shokubai
*10 Polyquaternium-39: Merquat Plus 3330 available from Calgon
*11 Polyquaternium-47: Merquat 2001 available from Calgon
*12 Carbomer 1: Carbopol 981 available from B. F. Goodrich
*13 Carbomer 2: Carbopol Ultrez 10 available from B. F. Goodrich
*14 Dimethicone and Dimethiconol: DCQ2-1403 available from Dow Corning
*15 Cyclomethicone/Dimethicone: Gum/Cyclomethicone blend available from Shin-Etsu
*16 Dimethicone: Dimethicone Fluid CF330M available from General Electric Silicones
*17 Hexylene Glycol: Hexylene glycol available from Mitsui Toatsu
*18 Polygonum multiflora extract: Polygonum multiflora extract obtained from Occupational Medicine, CAPM.
*19 Vitamin E: Emix-d Available from Eisai
*20 Panthenol: Panthenol Available from Roche
*21 Visible particles 1: Unispheres AGE-527 available from Induchem
*22 Visible particles 2: Unispheres YE-501 available from Induchem.
*23 Cetyl hydroxyethylcellulose: Polysurf 67 available from Aqualon
*24 Hydroxyethylcellulose: NATROSOL available from Hercules
*25 Polyquaternium-22: Merquat 280 available from Calgon
*26 Oleyl Alcohol: UNJECOL 90BHR available from Shin Nihon Rika
*27 Pentaerythritol Tetraisostearate: KAKPTI available from Kokyo Alcohol
*28 Aloe Extract: Aloe Extract Vera available from Ichimaru Farcos.
*29 Ginseng: Ginseng available from Occupational Medicine, CAPM Method of Preparation The carboxylic acid/alkyl carboxylate copolymer and additional viscosity modifier, if present, are dispersed in water at room temperature, mixed by vigorous agitation, and then heated to about 50° C. A triblender can be used if necessary to disperse the polymeric materials. The obtained mixture is cooled to below 40° C. and then the neutralizing agent is added to the mixture. After neutralizing, the remaining components, including amphoteric polymer, are added to the mixture.

Examples 1 through 16 are hair conditioning compositions of the present invention which are particularly useful for leave-on use. These examples have many advantages. For example, they can provide improved conditioning benefits to the hair such as moisturized feel, are easy to apply on the hair, and leave the hair and hands with a clean feeling.

It is understood that the examples and embodiments described herein are for illustrative purposes only and that various modifications or changes in light thereof will be suggested to one skilled in the art without departing from its spirit and scope.

What is claimed is:

1. A hair conditioning composition comprising:
   (1) from about 0.01% to about 10% of a carboxylic acid/carboxylate copolymer;
   (2) from about 0.1% to about 10% of a polypropyleneglycol moisturizing agent
   (3) from about 0.05% to about 5% of an amphoteric polymer; and (4) an aqueous carrier.

2. The hair conditioning composition according to claim 1 further comprising from about 0.1% to about 10% of a silicone compound selected from the group consisting of Dimethicone fluid, Dimethicone gum, Dimethiconol fluid, and mixtures thereof.

3. The hair conditioning composition according to claim 1, further comprising from about 0.1% to about 5% of a low melting point oil.

4. The hair conditioning composition according to claim 1 further comprising from about 0.01% to about 5% of an additional viscosity modifier.

5. The hair conditioning composition according to claim 1 further comprising from about 0.01% to about 5% of a visible particle.

6. The hair conditioning composition according to claim 1 further comprising from about 0.01% to about 2% of an herbal extract.

7. A method of making a hair conditioning comprising the steps of:
   (a) neutralizing the carboxylic acid/carboxylate copolymer with a neutralizing agent in an aqueous carrier; and
   (b) adding an amphoteric polymer and a moisturizing agent selected from the group consisting of polypropylene glycol, oleth-5, oleth-3, steareth-5, steareth-4, ceteareth-5, ceteareth-4, ceteareth-3, mixtures of $C_{9-11}EO5$, mixtures of $C_{9-11}EO2.5$, mixtures of $C_{12-13}EO3$, mixtures of $C_{11-13}EO5$, and mixtures thereof, to an obtained mixture.

8. A hair conditioning composition comprising:
   (1) from about 0.01% to about 10% of a carboxylic acid/carboxylate copolymer;
   (2) from about 0.1% to about 10% of a moisturizing agent selected from the group consisting of oleth-5, oleth-3, steareth-5, steareth-4, ceteareth-5, ceteareth-4, ceteareth-3, mixtures of $C_{9-11}EO5$, mixtures of $C_{9-11}EO2.5$, mixtures of $C_{12-13}EO3$, mixtures of $C_{11-13}EO5$, and mixtures thereof;
   (3) from about 0.05% to about 5% of an amphoteric polymer; and
   (4) an aqueous carrier.

* * * * *